United States Patent [19]

Shumway et al.

[11] Patent Number: 4,855,440

[45] Date of Patent: Aug. 8, 1989

[54] METHOD FOR PRODUCING STABLIZED IMIDAZOLINE DERIVATIVES

[75] Inventors: Dale F. Shumway; Harry C. Robbins, both of Janesville, Wis.

[73] Assignee: Sherex Chemical Company, Inc., Dublin, Ohio

[21] Appl. No.: 155,768

[22] Filed: Feb. 16, 1988

[51] Int. Cl.$^4$ .................................. C07D 233/04
[52] U.S. Cl. ........................... 548/353; 548/347; 548/352
[58] Field of Search ............... 548/347, 352, 353

[56] References Cited

U.S. PATENT DOCUMENTS 3,468,904 9/1969 Kritchevky .................. 548/352
4,189,593 2/1980 Wechsler et al. .............. 548/352

Primary Examiner—Mary C. Lee
Assistant Examiner—J. Richter
Attorney, Agent, or Firm—Mueller and Smith

[57] ABSTRACT

Disclosed is a method for stabilizing the color of liquid imidazolines which comprises pre-treating a polyamine with an effective amount of a hydride, preferably a borohydride, followed by its reaction with a fatty acid or ester thereof under amide-forming reaction conditions to make an amide intermediate, followed by subjecting said amide intermediate to imidazoline-forming reaction conditions to make said color-stablized imidazoline product.

9 Claims, No Drawings

METHOD FOR PRODUCING STABLIZED IMIDAZOLINE DERIVATIVES

BACKGROUND OF THE INVENTION

Imidazolines are a family of compounds based on a five-membered ring structure containing two nitrogen atoms and a double bond. The ring is numbered in such fashion that the nitrogens carry the lowest combination of numbers:

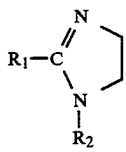

Commercially, imidazolines are made from the reaction of fatty acid, fatty alkyl (e.g. methyl) esters, or fatty triglycerides with a polyamine such as diethylenetriamine (DETA), aminoethylethanolamine (AEEA), ethylenediamine (EDA), or triethylenetetramine (TETA). The intermediate amidoamine is dehydrated to yield the cyclic imidazoline product.

While the manufacture of imidazolines on a commercial scale is relatively easy, the product is not easy to store or use without hydrolysis. Numerous authors have commented on the instability of the imidazoline molecule. Linfield, *JAOCS*, 61, No. 2 (1984), p 439, states that the imidazolines are unstable and in the presence of water revert back to the amidoamine starting material by standing overnight at room temperature. Wechsler, et al., U.S. Pats. Nos. 4,269,730 and 4,189,593, caution that during the reduced pressure dehydration to make the imidazoline, care must be taken to avoid any contact between the reactant and air which would cause rapid and severe darkening of the product. Butler, et al., *J. Chem. Res.*, (5), 84 (1981) report decomposition of the imidazoline ring under atmospheric conditions in 2-9 days provided the compound contains a cis-olefin system. Bristline, et al., *JAOCS*, 60, No. 4 (1983), p 823, showed that the imidazoline ring content in a system decreased from 38% to 6% imidazoline in 72 hours with the addition of 2% $H_2O$ (half-life of 24 hours). Even in a sealed container, these authors reported 5–8% loss in ring content over 18 months. Their conclusion was that, "When used as intermediates, imidazolines should be reacted promptly and prolonged storage should be avoided". Bristline, et al., *JAOCS*, 60, (1983), p 1676, showed that, "The imidazoline is hydrolyzed quantitatively to the diamide in the presence of water in ca. four days at room temperature."

This well-documented hydrolytic instability has inhibited the commercialization of imidazolines for aqueous applications. When imidazolines are protonated or quaternized, however, their hydrolytic stability is dramatically increased as is their water compatibility. Commercial producers, then, often manufacture the protonated or quaternized derivatives of imidazolines. Imidazoline-derived amphoterics, such as the chloroacetate derivative, are known to be excellent foamers and good cleaners, yet are substances of low toxicity possessing properties of low-irritancy to both skin and eye. Hunting, "Amphoteric Surfactants", *Cosmetics & Toiletries*, 95, November 1980, p 95, and references cited therein, reports that these amphoterics also are bacteriostatic.

Broad Statement of the Invention

The present invention is directed to an imidazoline product which is light-colored and color-stabilized. Broadly, imidazolines are made by reacting a polyamine and a fatty acid or ester thereof under amide-forming conditions followed by the establishment of imidazoline-forming conditions to convert the amide intermediate into the desired imidazoline product. The present invention comprises pre-treating the polyamine reactant with an effective amount of a hydride prior to the amide-forming reaction. The resulting stabilized imidazoline product can be handled and stored as a liquid under conventional liquid imidazoline-storage conditions for a sufficient time to permit the product to be shipped from the manufacturing site to another location whereat the imidazoline product is to be used. This time period can range from a few days to 10–14 days. While some color loss is exhibited by the stored imidazoline product of the present invention, since the manufactured liquid imidazoline product is color-stabilized and is lighter in color by dint of the hydride pre-treatment, the stored product does not degrade as much as a conventional counterpart product without the pre-treatment. Users of the product, then, will be dealing with a lighter colored product, giving them a wide number of choices with respect to use of the product in final formulations. These and other advantages will be readily apparent to those skilled in the art based upon the disclosure contained herein.

DETAILED DESCRIPTION OF THE INVENTION

Imidazolines are manufactured, stored, and transported in the substantial absence of oxygen for minimizing color degradation of the product. Good quality nitrogen can contain up to 2% oxygen while liquid nitrogen normally contains about 10 ppm oxygen or thereabouts. Even using liquid nitrogen as the source for the gas blanket which fills the headspace in the container, the imidazoline liquid product will lose color over time. Thus, little commercial use of imidazolines is made, with the preference being to utilize more stable derivatives thereof as described above. It is not unusual for the manufacturing and the use situses to be located quite a distance apart, thus necessitating transportation and storage times of a few days to a few weeks being required of the imidazoline liquid product. By stabilizing the imidazoline liquid product against color degradation, the formulator will be presented a lighter colored product, thus enabling the formulator to dye the final formulation to a pleasing appearance. Moreover, the imidazoline product can be converted into a variety of final forms including, for example, an amine salt in situ when dispersed in acid aqueous solutions in the formulation of fabric softener dispersions. The stabilized imidazoline liquid products also can be added to anionic compounds without fear of complexing, thus offering the opportunity to develop unique detergency/softening/anti-static properties not obtained when anionic/cationic complexes are used, for example, in laundry products.

Unexpectedly, it was discovered that hydride treatment of the polyamine reactant ameliorates the unstable appearance which the imidazoline product otherwise displays without such treatment. It is not readily apparent how the hydride treatment functions, though a precipitate often is formed and is believed to be a hydride/polyamine contaminant product. Nevertheless, once the hydride treatment has been effectively administered, the stabilized imidazoline product is relatively stable in the presence of atmospheric oxygen.

With respect to the hydride treatment, initially it was felt that addition of hydride to the polyamine/fatty acid (or ester) reaction mixture would be a convenient means for stabilizing the resultant imidazoline product. This procedure, using borohydride as disclosed in U.S. Pat. No. 3,468,904, however, turned out to be not as effective, as the resulting imidazoline product still darkened to an undesirable extent. Rather, it was unexpectedly discovered that pretreatment of the polyamine reactant prior to establishing amide-forming reaction conditions resulted in an imidazoline product which was more color stable. Some fatty acid ester reactant can be present during this pretreatment, though reaction conditions are established such that the temperature is less than that required for amide formation, e.g. a temperature of less than about 100° C. Following the polyamine hydride pretreatment, the fatty acid ester reactant (or remaining fatty acid ester reactant) is combined with the pretreated polyamine and amide-forming reaction conditions established. Amide-forming reaction conditions comprehend a temperature in excess of 100° C. and usually in the range of about 125° C. to 300° C. for reaction times ranging from about 4 to 12 hours. After the amide intermediate has formed, application of vacuum with resultant water distillation from the reaction mixture results in the formation of the cyclic imidazoline product.

The resulting product can be used as is or any precipitate formed as a result of the hydride pretreatment can be removed therefrom. The color stable imidazoline product can be stored and used as is, can be converted to a variety of derivatives, of can be transformed into a variety of product configurations. These product configurations include conventional atomization techniques for forming beads or powder of the imidazoline product, use of chilled rolls for forming sheets of imidazoline product which then may be broken up for forming flakes, or any other conventional technique, such as disclosed in commonly-assigned U.S. Ser. No. 278,200, filed Oct. 21, 1988.

A wide variety of hydrides can be used in accordance with the present invention. Referring to borohydrides useful in the present invention, borohydrides typically fall into the groups of alkali metal borohydrides, alkaline earth metal borohydrides, quaternary ammonium borohydrides, and amine borohydrides. Illustrative examples include the borohydrides of sodium, potassium, lithium, calcium, barium, magnesium, strontium, and lithium-aluminum; tetramethyl ammonium borohydride, tetraethyl ammonium borohydride, tetrapropyl ammonium borohydride, and tetraisopropyl ammonium borohydride; triethylamine borohydride, triisopropylamine borohydride, tri-butylamine borohydride, and triisobutylamine borohydride. The quantity of borohydride required typically ranges from about 0.005 to about 1% with quantities from about 0.1 to about 0.5% typically being effective (bias polyamine being pretreated). It should be borne in mind that the quantity of borohydride may be correlated to the polyamine contaminant content.

Additional hydrides which find use in accordance with the present invention include saline hydrides, e.g. alkali metal and alkaline earth metal hydrides; lithium aluminum hydride and related aluminum hydride materials; and the like and even mixtures thereof. Those skilled in the art will appreciate that an extensive list of hydrides is known and can be used in accordance with the precepts of the present invention.

With respect to imidazolines, the literature is replete in descriptions of suitable polyamines and suitable fatty acids or esters thereof useful in imidazoline formation. Briefly, fatty acids typically are monobasic aliphatic acids containing from about 8 to 30 carbon atoms and more often from about 12 to 22 carbon atoms. Typically, fatty acids are derived from natural triglyceride sources, e.g. vegetable oils, though they may be derived from animal, fish, or nut oil, or they may be synthetic in nature. Esters of such fatty acids also can be used as is well known in the art.

Briefly, polyamines useful in making imidazolines include ethylene diamine, diethylene triamine, triethylene tetramine, aminoethylethanol amine, hydroxyethyl diethylene triamine, and the like and mixtues thereof. The foregoing list of fatty acids and polyamines merely is exemplary of the broad nature of imidazolines which can be stabilized in accordance with the precepts of the present invention. Anti-oxidants and/or sequestrants can be used in the stabilized imidazoline product as is necessary, desirable, or convenient in conventional fashion.

The following examples show how the present invention has been practiced but should not be construed as limiting. In this application, all percentages and proportions are by weight unless otherwise expressly indicated. Also, all citations disclosed herein are expressly incorporated herein by reference.

EXAMPLES

Example 1

N-1-hydrogenated tallow amido ethyl-2-hydrogenated tallow imidazoline was made with the borohydride polyamine pre-treatment from the following ingredients:

| Ingredient | Quantity | |
|---|---|---|
| | Moles | Wt % |
| Diethylene Triamine (DETA) | 1.00 | 15.18 |
| Hydrogenated Tallow | 0.667 | 84.75 |
| Sodium Borohydride | — | 0.07 |

DETA was charged to a clean, dry reactor and heated to 200° F. and the sodium-borohydride added thereto. The reactor was evacuated to 10-20 mm Hg vacuum and purged to 15 psig with nitrogen. The hydrogenated tallow was charged to the reactor and its contents heated to 280°-290° F. The amide cook was continued for four hours until a neutralizing equivalent of 590-620 and an ester/amide ratio of 0.06/1 maximum was achieved. Thereafter, the reactor was evacuated to 15-20 mm Hg vacuum and heated to 400° F. as fast as possible. The amide in the reactor was stripped at 15-20 mm Hg vacuum and 400°-420° F. maximum temperature for two hours until percent tertiary amine was 94% minimum. The reactor then was purged with additional nitrogen and cooled to 190°-200° F. for storage and handling.

EXAMPLE 2

In order to study the effects of oxygen on the imidazolines, varying proportions of oxygen were added to the nitrogen blanketing gas utilized during the imidazoline formation reactions. The proportion of oxygen ranged from less than 10 ppm to about 2% by volume. The effect of the borohydride treatment with respect to degradation of the color of the imidazoline product in the presence of oxygen was studied. Batches made with the novel polyamine hydride pre-treatment were made along with comparative batches where no treatment occurred as well as where borohydride was added during the cook as disclosed in U.S. Pat. No. 3,468,904. The same ingredients were utilized as set forth in Example 1 except that an anti-oxidant also was included in the reaction ingredients along with an anti-foam agent. The following results were recorded:

TABLE 2

| | IMIDAZOLINE GARDNER COLOR | | |
|---|---|---|---|
| $O_2$ (wt %) | Control | Inventive Polyamine Pre-Treatment | '904 Simultaneous Addition |
| 10 ppm | 3− | 1 | 2,2,2− |
| 0.15 | — | 2,2− | 3−,3+ |
| 0.50 | — | 2− | 3+,4− |
| 2.0 | — | 4−,4+ | 4+ |

The 10 ppm oxygen runs represent the level of oxygen in nitrogen often encountered in manufacturing plant settings. The data shows that the inventive pre-treatment run 195-187 resulted in a better color quality product than comparative runs 195-155, 166, 167 which utilized the simultaneous addition of borohydride to the reactant mixture. Both borohydride treatments were better than Control 195-171 wherein no hydride treatment was used.

At 0.15 vol-% oxygen in the nitrogen blanket, inventive polyamine pre-treatment runs 195-189 and 190 again provided a lighter colored product than comparative hydride treatment runs 195-174 and 177. Again at 0.5 vol-% oxygen level, inventive run 195-193 again provided a much lighter color product than did comparative hydride runs 195-162 and 164. It will be observed that the comparative hydride runs are resulting in an imidazoline product which is deteriorating in color at a greater rate than the inventive polyamine pre-treated samples.

Finally, it appears that at 2.0 vol-% oxygen, inventive samples 195-191 and 192 resulted in products which were about equivalent in color with comparative hydride treated sample 195-165. These results suggest that the level of oxygen exceeded that level whereat the hydride treatment of the present invention is more effective than the comparative hydride treatment of the art. As noted above, such an oxygen level is far beyond that which is normally encountered in typical commercial settings which utilize nitrogen blanketing operations.

We claim:

1. In a method for making an imidazoline liquid product of improved color stability by reacting a polyamine and a fatty acid or ester thereof under amide-forming reaction conditions comprising a temperature ranging from between about 100° and 300° C. and an inert atmosphere, to make an amide intermediate followed by subjecting said amide intermediate to imidazoline-forming reaction conditions comprising reduced atmospheric conditions with provision for removal of water, the improvement which comprises pre-treating said polyamine at a temperature of less than about 100° C. with an effective amount of a hydride prior to its reaction with said fatty acid or ester thereof.

2. The method of claim 1 wherein said hydride comprises a borohydride.

3. The method of claim 1 wherein the proportion of said hydride ranges from about 0.005 to about 1% by weight of said polyamine.

4. The method of claim 2 wherein the proportion of said borohydride ranges from about 0.005 to about 1% by weight of said polyamine.

5. The method of claim 2 wherein said borohydride comprises an alkali metal or alkaline earth metal borohydride.

6. The method of claim 1 wherein said inert atmosphere comprises nitrogen gas containing less than about 0.5% oxygen.

7. The method of claim 1 wherein the polyamine which is pretreated is selected from the group consisting of ethylene diamine, diethylene triamine, triethylene tetraamine, aminoethylethanol amine, hydroxyethyl diethylene triamine, and mixtures thereof.

8. The method of claim 1 wherein said fatty acid comprises a $C_8$–$C_{30}$ aliphatic fatty acid or a $C_1$–$C_{30}$ alkyl ester thereof.

9. The method of claim 8 wherein said fatty acid ester comprises a triglyceride.

* * * * *